United States Patent [19]

Huffman

[11] Patent Number: 5,775,899
[45] Date of Patent: Jul. 7, 1998

[54] DENTAL MODEL BASE HAVING INTEGRAL PINS

[76] Inventor: Ronald E. Huffman, Rte. 1, Box 502M, Sapulpa, Okla. 74066

[21] Appl. No.: 551,559

[22] Filed: Nov. 1, 1995

[51] Int. Cl.⁶ ............................................. A61C 11/00
[52] U.S. Cl. ................................................ 433/60; 433/74
[58] Field of Search ............................... 433/74, 60, 213

[56] References Cited

U.S. PATENT DOCUMENTS

| | | | |
|---|---|---|---|
| 1,745,570 | 2/1930 | Dimelow | 433/202.1 |
| 1,780,117 | 10/1930 | Craigo | |
| 2,398,671 | 4/1946 | Saffir | 433/208 |
| 2,585,857 | 2/1952 | Schwartz | |
| 3,453,736 | 7/1969 | Waltke | |
| 3,518,761 | 7/1970 | Susman et al. | |
| 3,937,773 | 2/1976 | Huffman | 264/17 |
| 3,969,820 | 7/1976 | Kulig et al. | |
| 4,021,916 | 5/1977 | Spalten | |
| 4,122,606 | 10/1978 | Roman | |
| 4,127,939 | 12/1978 | Samuel et al. | |
| 4,203,219 | 5/1980 | Wiener | 433/74 |
| 4,242,812 | 1/1981 | Randoll et al. | 434/263 |
| 4,265,619 | 5/1981 | Lucki et al. | 433/74 |
| 4,371,339 | 2/1983 | Zeiser | 433/74 |
| 4,382,787 | 5/1983 | Huffman | 433/64 |
| 4,398,884 | 8/1983 | Huffman | 433/74 |
| 4,443,192 | 4/1984 | Blitz | 433/74 |
| 4,459,110 | 7/1984 | Jackson | 433/74 |
| 4,521,188 | 6/1985 | Metzler | 433/74 |
| 4,608,016 | 8/1986 | Zeiser | 433/74 |
| 4,708,835 | 11/1987 | Kiefer | 264/17 |
| 4,721,464 | 1/1988 | Roden et al. | 433/74 |
| 4,767,331 | 8/1988 | Hoe | 433/213 |
| 4,898,359 | 2/1990 | Gopon | 433/74 |
| 5,028,235 | 7/1991 | Smith | 433/223 |
| 5,049,075 | 9/1991 | Barrut | 433/196 |
| 5,098,290 | 3/1992 | Honstein et al. | 433/74 |
| 5,197,874 | 3/1993 | Silva et al. | 433/74 |
| 5,207,574 | 5/1993 | Garland | 433/74 |
| 5,352,117 | 10/1994 | Silva | 433/60 |
| 5,393,227 | 2/1995 | Nooning | 433/74 |
| 5,466,152 | 11/1995 | Walter | 433/60 |

FOREIGN PATENT DOCUMENTS

| | | |
|---|---|---|
| 0 151 086 | 1/1985 | European Pat. Off. |
| 0 291 821 | 5/1988 | European Pat. Off. |
| 0 528 335 | 8/1992 | European Pat. Off. |
| 3436 094 | 3/1985 | Germany |
| 3505 680 | 7/1985 | Germany |
| 3521 137 | 12/1986 | Germany |
| 3825 014 | 1/1990 | Germany |
| 866118 | 4/1961 | United Kingdom |
| WO 88/10101 | 12/1988 | WIPO |

OTHER PUBLICATIONS

International Search Report mailed Apr. 1, 1997.
Instruction Booklet, DVA Model & Die System, "Instructions for Use", DNA, Inc.
Instructional Guide, Step by Step, Die–Maker W.O.W. Articulator, Accu Bite, East Lansing, Michigan.
Brochure, "Die–Maker W.O.W. Articulator", Accu Bite.

*Primary Examiner*—Cary E. O'Connor
*Attorney, Agent, or Firm*—Merchant, Gould, Smith, Edell, Welter & Schmidt

[57] ABSTRACT

A premanufactured dental model base is disclosed for supporting a cast dental model. The dental model base has preformed integral pins adaptable for securing the dental model to the dental model base and for disengageably retaining a dental model segment representing a damaged tooth.

8 Claims, 4 Drawing Sheets

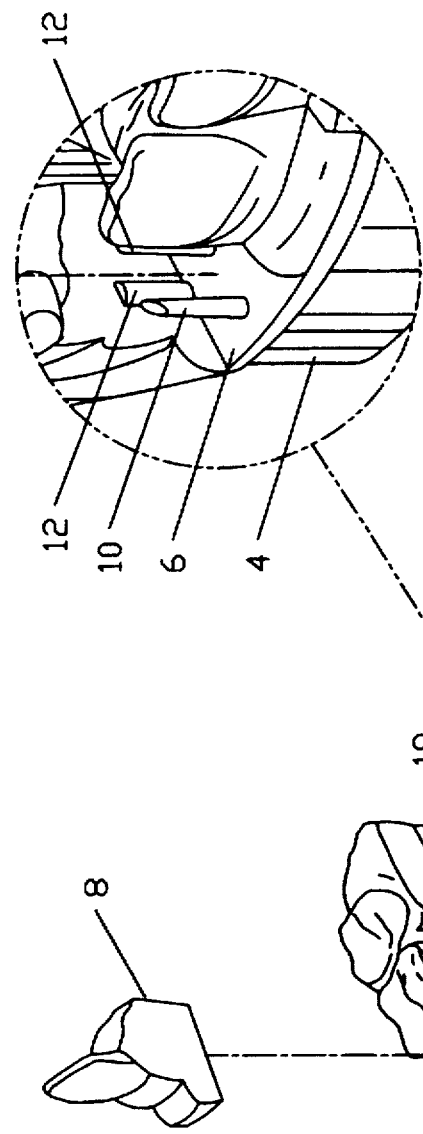
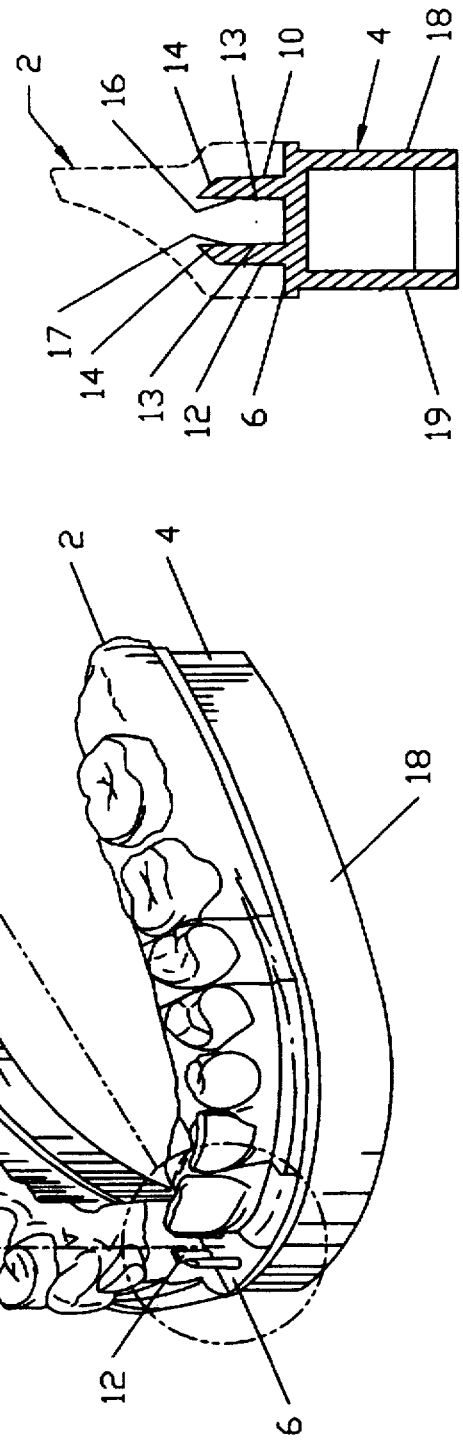

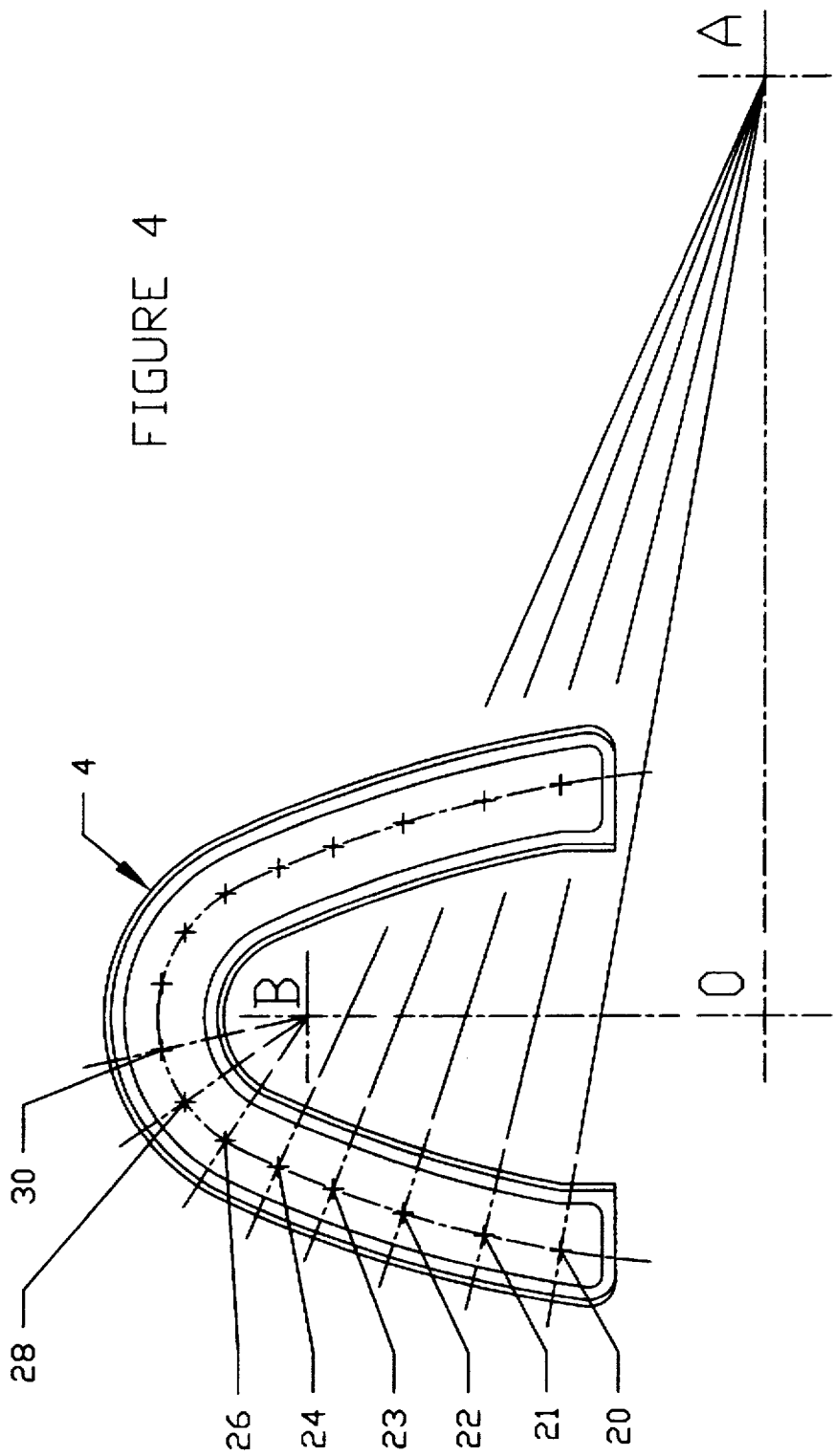

DENTAL MODEL BASE HAVING INTEGRAL PINS

BACKGROUND

This invention relates generally to a dental model base, and more particularly, to a premanufactured base having a plurality of pins formed and positioned to support a dental model.

Damaged teeth may be repaired or replaced by crowns, bridge inlays or other common dental prostheses. A successful repair requires accurate alignment and visual uniformity of the repaired tooth with the patient's other teeth. Typically, a model is made of the patient's teeth and the prosthesis is fitted to the model and adjusted to achieve proper alignment and visual uniformity.

The model is typically formed by having a patient bite into a pliant casting material which cures to create a mold cavity having a negative impression of the patient's teeth and gums. The mold can be of all or any portion of the patient's gum line. A castable material is then poured into the negative impression to create a stone replica or dental model of the patient's teeth and gums.

To facilitate prosthesis development, the replica of the damaged tooth or teeth is severed from the remainder of the dental model. Severability is typically achieved by positioning the knurled end of a tapered metal dowel in the uncured stone material in correspondence with the damaged tooth or teeth. The metal dowel or dowels must be carefully aligned and held in position which requires skill and time. Once the casting of the gum and teeth has hardened, the cured dental model is positioned adjacent an uncured dental model base which is held in a dental base mold. The tapered portion of the dowels protruding from the dental model is positioned in the uncured dental model base. To prevent bonding with the dental model base, wax may be placed between the base and the dental model and around the tapered portion of the dowels.

Once the dental model base has cured, a saw cut on each side of the damaged tooth model is made down to the dental model base which allows removal of the damaged tooth model and the attached dowel from the rest of the dental model. Once the damaged tooth model is removed, the prosthesis can be fitted and adjusted without the spacial limitations encountered when the damaged tooth model is joined to the full dental model. After the prosthesis is made and attached to the dental model segment, the tapered dowel attached to the dental model segment is guided into its respective aperture in the dental model base which guides the dental model segment to its position in the dental model. Alignment and visual conformity are then assessed.

Alignment is ascertained by evaluating the registration of the repaired tooth with the dental model of the patient's opposing teeth. This is achieved by connecting the upper and lower dental model with an articulator. If the prosthesis is out of alignment or does not visually conform to the rest of the patient's teeth, the dental model segment containing the damaged tooth can be removed, adjusted and returned to the dental model base. This process is repeated until proper alignment and visual conformity is achieved. Thus, the model of the damaged tooth may be repeatedly engaged and disengaged with the dental model base.

The above described process requires time for the dental model and dental model base castings to cure. The dental model shrinks as it cures, which adversely affects the accuracy of the model. Also, skill and time are both required to accurately place the dowels in the dental model. Any misalignment may result in an unusable casting. For example, if the dowels are misaligned the dental model segment may be unseverable from the dental model. Also, if the dowel is located in the saw path between the dental model and the portion to be severed, the saw cut will either sever the dowel or render it ineffective for securing the dental model segment. Thus, considerable time must be spent achieving proper alignment and allowing the dental model base casting to cure.

Some dental model bases are fabricated from plastic. In one version, a technician must drill a tapered aperture in the dental model base to accommodate the placement of the dowel in the dental model casting. Skill and time are required to align the dowel with the damaged tooth model and the plastic base and to accurately drill the tapered aperture which receives the tapered dowel.

Another available plastic dental model base has a plurality of pre-formed apertures for receiving metal dowels which eliminate the above-mentioned drilling step. However, the apertures are not positioned to correspond with normal tooth placement. Thus, skill is still required to accurately align the dowels with the dental model.

Also, in existing full arch plastic bases, plastic extends from the right molars to the left molars, creating a platform for excess casting material in the lingual area. It may be desirable to remove this excess casting material as part of the model preparation process. The plastic platform interferes with this removal step. The platform may also impair assessment of visual conformity.

In summary, conventional dowels may be accurately aligned with the damaged tooth in a cast dental model base; however, the casting and alignment procedure takes time and requires skill. Plastic bases avoid the expense of casting a dental model base but may require additional steps, such as drilling for accurate placement of a dowel within the dental model. If the plastic base has preformed apertures for dowel placement, the apertures may not correspond to normal tooth placement and skill is required to accurately place the dowels within the dental model.

As mentioned above, metal dowels are typically used to detachably engage a dental model segment to the dental model base. However, metal dowels are undesirable in some circumstances. For example, porcelain facings are often created to repair damaged teeth. The green porcelain material is applied to a damaged tooth model and the dental model segment containing the tooth model is heated to set or cure the porcelain material. The porcelain heating temperature is elevated and will adversely affect typical metal dowels.

Therefore, what is needed is a preformed dental model base that does not require time-consuming and skillful alignment with the dental model. Such a base would eliminate the need to pour a dental model base while reducing the skill and time required to accurately align the base with the dental model. Such a base would also restrain the curing model, thereby reducing shrinkage. Removal of the platform in the lingual area would be an additional improvement, giving technicians improved access to the dental model, facilitating removal of excess casting material in the lingual area and enhancing assessment of visual conformity. Still another improvement would provide a dental model base adapted for supporting a dental model while permitting the disengageable connection of a dental model segment to the dental model base without using metal dowels.

SUMMARY

The present invention is directed to an apparatus and method which satisfy the need for a preformed dental model base. In one embodiment, the base has a plurality of preformed pins adapted to detachably connect a dental model segment to the dental model base. In an alternative embodiment, the pins are integrally formed with the dental model base. In yet another embodiment, the preformed pins are positioned to correspond to normal tooth placement.

The dental model base comprises a premanufactured dental model base body. The base body has a plurality of preformed pins extending from a dental model support surface into a dental model. The preformed pins have a cross-section adapted for detachably engaging a dental model segment. In another embodiment, a method for using a dental model base is provided.

Some advantages provided by these embodiments are:

1. Time savings resulting from not casting the dental base;
2. Preformed pins corresponding to normal tooth placement eliminate the need for skillful placement of the pins in the dental model, thereby saving time and requiring less skill;
3. A full arch base body having a convenient U-shape which allows for removal of excess casting material in the lingual area, improves access to the dental model and enhances assessment of visual conformity;
4. A shape corresponding to the normal shape of a patient's gum line;
5. A transparent base that aids assessment of visual conformity;
6. A rigid plastic base that helps minimize shrinkage of the cast dental is model;
7. A dental model base body formed with integral pins thereby eliminating the need for metal dowels; and
8. Dental model segments ready for enamel application.

Other advantages and features will become apparent from the following description and from the claims.

BRIEF DESCRIPTION OF THE DRAWINGS

FIG. 1 is a perspective view of a full arch dental model base body and attached dental model according to the present invention.

FIG. 2 is an enlarged perspective top plan view of a portion of a full arch dental model base body and attached dental model according to the present invention.

FIG. 3 is a cross sectional view of a dental model base and attached dental model according to the present invention.

FIG. 4 is a plan view of a full arch dental model base body according to the present invention.

DESCRIPTION OF THE PREFERRED EMBODIMENTS

Figure 5:
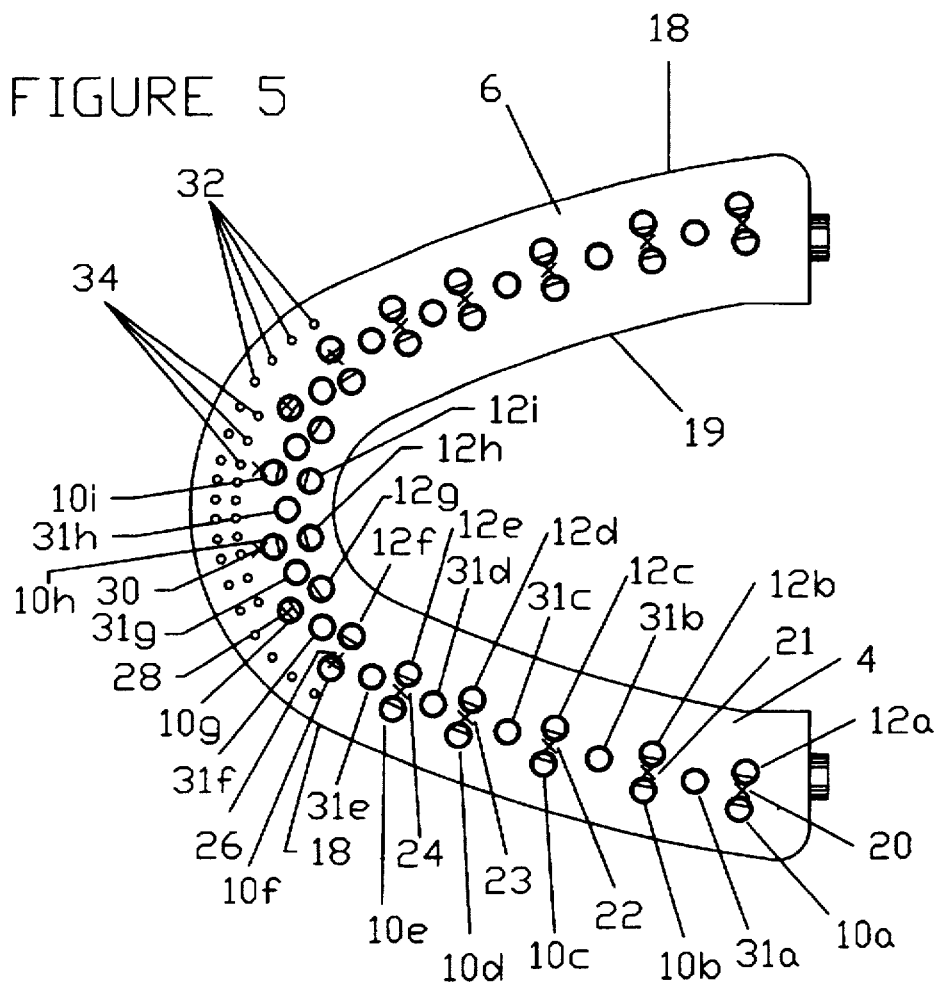
FIG. 5 is a plan view of a full arch dental model base body according to the present invention.

FIG. 1 depicts a full arch dental model 2 supported by one embodiment of a dental model base body 4 according to the present invention. FIG. 2 is an enlarged view of a section of the full arch dental model and base body depicted in FIG. 1. In this embodiment, a clear acrylic plastic is preferred for the dental model base body 4, however, many other materials may be used. The dental model 2 is adjacent the dental model support surface 6 which defines one surface of the dental model base body 4. Saw cuts through the dental model 2 on either side of the model of a damaged tooth allow removal of a dental model segment 8. A plurality of exterior pins 10 and a plurality of interior pins 12 are integrally formed with the dental model base body and extend approximately 8 mm from the dental model support surface 6. The axes of pins 10 and 12 are generally perpendicular to the dental model support surface 6. The pins 10 and 12 are detachably engaged with the dental model segment 8.

FIG. 3 depicts a cross-sectional view of a dental model base body 4 supporting a dental model 2. Exterior pins 10 and interior pins 12 extend into apertures 13 formed in the dental model 2. The pins 10 and 12 are tapered such that their cross-sectional area is greatest near the dental model support surface 6. The pins 10 and 12 have a diameter of approximately 3 mm near the dental model support surface 6 and a diameter of approximately 2.4 mm at the end remote from the dental model support surface 6. The distal ends of the exterior pins 10 and interior pins 12 terminate in a tapered surface 14. Such tapered surface (or cant) 14 slopes upwardly toward the interior side 16 of the exterior pins 10 and the exterior side 17 of the interior pins 12.

A multitude of pin placement patterns are within the scope of this invention. For example, a random pattern of pins could be as effective as a single row of strategically placed pins. The pin pattern should include sufficient pins so that at least two pins engage a dental model segment 8. One pin would be adequate if a means such as an indexing protrusion were provided to assure alignment of the dental model segment 8 with the dental model 2. The pin pattern depicted in FIGS. 1 and 2 has a row of exterior pins 10 and a row of interior pins 12. The center of normal teeth are disposed between the exterior and interior pins 10 and 12. Normal tooth placement is discussed below.

Through analysis of many dental models, it was discovered that certain geometric relationships exist in the location and arrangement of individuals' teeth. This discovery permits the arrangement and location of apertures in a model base body to more closely conform to the actual location of teeth in a dental model. It has been determined that the buccal and lingual wall generally tend to have the same curvatures. Teeth are also generally located at the same point along the gum. However, tooth position may vary along the gum if one or more natural teeth are absent or if other abnormalities exist. While the curvature of the buccal and lingual wall remains fairly constant, the size of the gum varies. It has been determined that most gums can be characterized as small, medium or large.

The actual location of teeth along a normal gum can be determined by measuring the location of the center of teeth from a sampling of dental models with gums in the desired size range.

The measurements are then averaged to determine the average or normal position of teeth in the sample. The placement of the center of teeth in other size ranges and for lower teeth in all size ranges may be determined by following the same procedure.

FIG. 4 depicts a dental model base body 4 with a designation of the normal placement of the center of upper teeth on a medium-sized gum. The placement of normal teeth along a gum can be defined by certain points, lines, angles and dimensions, as follows. Points A and B are center points for radii useful for designating teeth placement. Line AO is perpendicular to line BO. Point O defines the intersection of lines AO and BO. Line BO bisects the dental model base body 4. Point A is 4.4668 inches to the right of point O.

The normal third molar center 20 is found by extending an arc with a 5.6598 inch radius from point A at a 9.75° angle clockwise from line AO and to the left of point A. The normal second molar center 21 is located by extending an arc of a 5.6598 inch radius from point A at a 13.5° angle clockwise from line AO and to the left of point A. The normal first molar center 22 is located by extending an arc with a 5.6598 inch radius from point A at an angle of 17.5° clockwise from line AO and to the left of point A. The normal second bicuspid center 23 is found by extending an arc with a 5.6598 inch radius from point A at a 21° angle clockwise from line AO and to the left of point A. The normal first bicuspid center 24 is found by extending an arc with a 5.5698 inch radius from point A at a 23.75° angle clockwise from line AO and to the left of A. Point B is 2.1443 inches up from point O along line BO. The normal cuspid center 26 is found by extending a 0.7054 inch radius from point B at an angle of 123° clockwise from and to the left of line BO. The normal lateral incisor center 28 is found by extending a 0.7054 inch radius from point B at a 145° angle clockwise from and to the left of line BO. The normal central incisor center 30 is found by extending an arc of a length of 0.7054 inches from point B at a 167° angle clockwise from and to the left of line BO.

Figure 6:
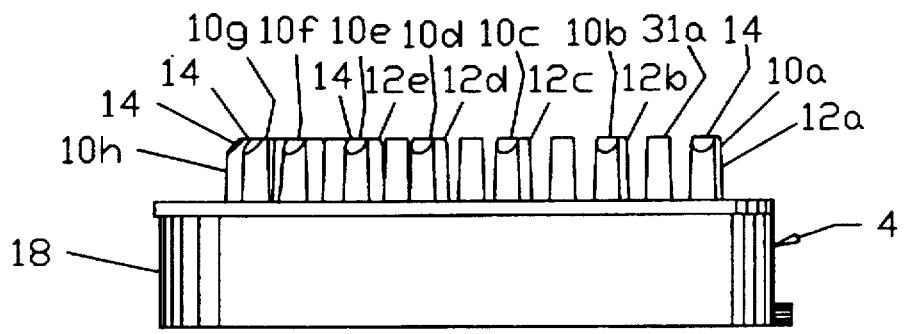
FIG. 6 is side elevation view of a full arch dental model base body according to the present invention.

FIGS. 5 and 6 depict an alternate embodiment of the present invention. In this embodiment, a row of medial pins 31 is interposed between the exterior pins 10 and the interior pins 12. The median pins 31 do not have a cant at the end remote from the dental model support surface 6.

The axis of an interior pin 12a is located approximately 2.5 mm on the interior side of the normal third molar center 20. The axis of exterior pin 10a is located approximately 2.5 mm on the exterior side of the normal third molar center 20. The axis of a median pin 31a is defined by extending an arc with a 5.6598 inch radius from point A at a 11.625° angle clockwise from line AO and to the left of point A.

The axis of an interior pin 12b is located approximately 2.5 mm on the interior side of the normal second molar center 21. The axis of an exterior pin 10b is located approximately 2.5 mm on the exterior side of the normal second molar center 21. The axis of a median pin 31d is at the point defined by an arc with a 5.6598 inch radius extending from point A at a 15.5° angle clockwise from line AO and to the left of point A.

The axis of an interior pin 12c is located approximately 2.5 mm on the interior side of the normal first molar center 22. The axis of an exterior pin 10c is located approximately 2.5 mm on the exterior side of the normal first molar center 22. The axis of a median pin 31c is at the point defined by extending an arc with a 5.6598 inch radius from point A at a 19.25° angle clockwise from line AO and to the left of point A.

The axis of an interior pin 12d is located approximately 2.5 mm on the interior side of the normal second bicuspid center 23. The axis of an exterior pin 10d is located approximately 2.5 mm on the exterior side of the normal second bicuspid center 23. The axis of a median pin 31d is at the point defined by extending an arc with a 5.6598 inch radius from point A at a 22.375° angle clockwise from line AO and to the left of point A.

The axis of an interior pin 12e is located approximately 2.5 mm on the interior side of the normal first bicuspid center 24. The axis of an exterior pin 10e is located approximately 2.5 mm on the exterior side of the normal first bicuspid center 24. Median pin 31e is disposed between pins 10 and 12e and 10 and 12f.

The axis of an interior pin 12f is located approximately 5.4 mm on the interior side of the normal cuspid center 26. The axis of an exterior pin 12f is located approximately 0.5 mm on the interior side of the normal cuspid center 26. A median pin 31f is disposed between pins 10 and 12f and 10 and 12g.

The axis of an interior pin 12g is located approximately 6.5 mm on the interior side of the normal lateral incisor center 28. The axis of an exterior pin 12g is located approximately 1.5 mm on the interior side of the normal lateral incisor center 28. A median pin 31g is disposed between pins 10 and 12g and 10 and 12h.

The axis of an interior pin 12h is located approximately 8 mm on the interior side of the normal central incisor center 30. The axis of an exterior pin 10h is located approximately 2.5 mm on the interior side of the normal central incisor center 30. A median pin 31h is disposed between pins 10 and 12h and 10 and 12i. Pins 10 and 12i mirror the placement of pins 10 and 12h.

These dimensions define the placement of pins for the left side of a full arch dental model base body 4. The right side of a full arch dental model base body 4 is a mirror image of the left side; therefore, the same geometric relationship will be used to define pin placement on the right side of the full arch dental model base body.

The exterior wall 18 is located approximately 16 mm from the center of the bicuspids and molars. The interior wall 19 is located approximately 7.5 mm inches from the bicuspids and molars. The distance of the exterior wall 18 from the center line of normal tooth placement increases to approximately 9 mm adjacent the central incisors. The distance from the interior wall to the central incisors increases to approximately 11.5 mm.

In the embodiment depicted in FIGS. 5 and 6, a row of first apertures 32 extends from cuspid to cuspid. The center of the first apertures are located approximately 3 mm from the exterior wall 18. A row of second apertures 34 extends from lateral incisor to lateral incisor. The centers of the second apertures 34 are located approximately 6 mm from the exterior wall 18. The first and second apertures 32 and 34 are adapted to slidingly engage a detachable pin (not shown). Detachable pins may be placed in the first and second apertures 32 and 34 if the patient's incisors are located radially outward from normal tooth placement. In an alternate embodiment, stone dowels (as discussed in co-pending application No. 08/477,541) may be formed to compensate for aberrant incisor placement.

Figure 7:
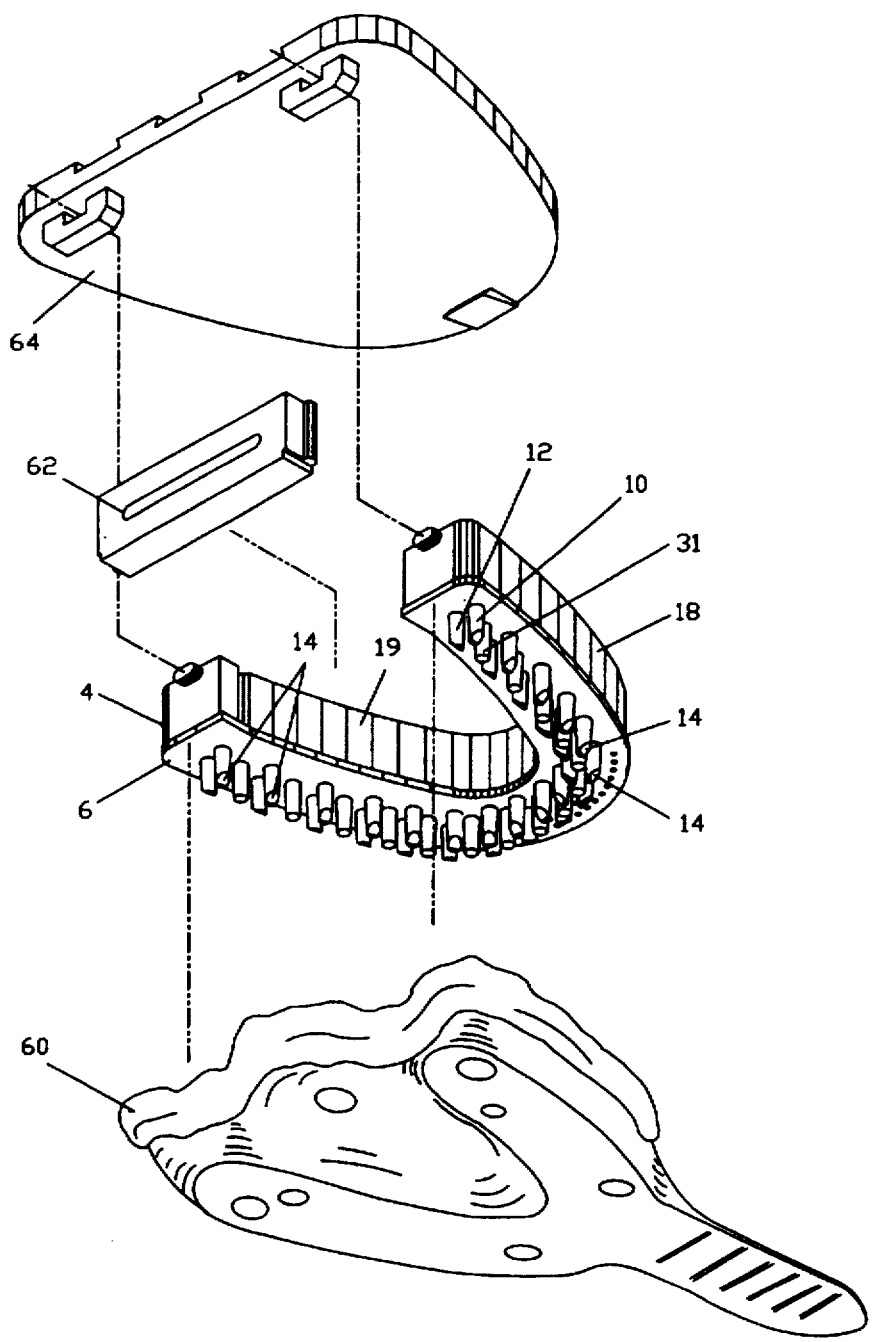
FIG. 7 is an exploded perspective view of a fully arch dental model base, articulator attachment plate, and articulator attachment bar and mold tray according to the present invention.

The present invention may be used as illustrated in FIG. 7. The mold tray 60 is filled with casting material and the dental model base body 4 is brought adjacent the mold tray 60. The mold tray 60, filled with casting material, is gently pressed against the dental model base body 4. The pins 10, 13 and 31 penetrate the casting material and form apertures 13 (see FIG. 3). If the patient's incisors or cuspids are outside their normal placement one or more detachable pins may be engaged with the first apertures 32 or the second apertures 34 prior to performing the process described above.

When the casting material hardens, the dental model 2 may be sawed on either side of a damaged tooth, as shown in FIG. 1. The saw-cut extends to the dental model support surface 6. Once the saw-cut has been completed, the dental model segment 8 of the damaged tooth can be removed by lifting it away from the dental model support surface 6 and the pins 10, 12 and 31. A nonadhesive, such as wax, may be applied to the dental model support surface 6 and pins 10, 12 and 31 adjacent the dental model segment 8 to facilitate disengagement of the dental model segment 8 with the dental model base body 4. Once the dental model segment 8 is removed, a prosthesis can be prepared to repair the damaged tooth. After the prosthesis is attached to the dental model segment 8, the dental model segment 8 can be returned to its place in the dental model 2. The pins 10, 12 and 31 align the dental model segment 8 with the dental model 2.

Once the dental model segment 8 has been returned to the dental model 2, the dental model base body 4 may be attached to an articulator with an articulator attachment bar 62 or an articulator attachment plate 64 as described in co-pending application Ser. No. 08/482,738 and registration is evaluated. If visual conformity is not achieved or if registration or alignment is improper, the dental model segment 8 containing the damaged tooth and prosthesis can be removed and the technician can adjust the prosthesis accordingly. This process is repeated until proper alignment and visual conformity is achieved.

The foregoing describes various embodiments of the claimed invention. The claimed invention is not limited to the embodiments described above. For example, it is contemplated that the principles of the invention described above can be applied to half arch dental model bases and quadrant dental model bases. It is also contemplated that this invention can be adapted for use with a variety of upper and lower gum sizes. Thus, numerous alternative constructions exist that would fall within the claimed invention.

What is claimed is:

1. A dental model base comprising:

a dental model base body, said dental model base body having an interior wall;

a dental model support surface adjacent said interior wall;

an exterior wall adjacent said dental model support surface;

a plurality of pins protruding from said dental model support surface, said pins being tapered, said sins having the greatest cross-sectional area near said dental model support surface; and an articulator attachment plate disengageably connected to said dental model base body.

2. The dental model base of claim 1 additionally comprising:

an articulator attachment bar engaging said dental model base body.

3. A dental model base comprising:

a dental model base body, said dental model base body having an interior wall;

a dental model support surface adjacent said interior wall;

an exterior wall adjacent said dental model support surface;

a plurality of pins protruding from said dental model support surface, said pins being tapered, having the greatest cross-sectional area near said dental model support surface; and an articulator attachment bar engaging said dental model base body.

4. A method comprising the steps of:

flowing an uncured casting material into a mold tray having a negative impression of a patient's teeth;

placing a dental model base body adjacent said mold tray, said dental model base body having a dental model support surface adjacent said uncured casting material in said mold tray, said dental model base body having a plurality of integral pins extending from said dental model support surface;

pressing said pins into said uncured casting material;

curing said casting material to form a dental model; and sawing through said dental model to said dental model support surface to separate a dental model segment from said dental model.

5. The method of claim 4, wherein:

said dental model base body has a plurality of apertures extending from said dental model support surface into said dental model base body.

6. The method of claim 5, additionally comprising the steps of:

engaging a detachable pin with one of said apertures;

placing said dental model base body with said detachably engaged pin adjacent said mold trays; and pressing said pins and detachably engaged pin into said casting material.

7. The method of claim 5, additionally comprising the steps of:

flowing said casting material into said apertures to form stone pins.

8. The method of claim 4 wherein:

a pin is cut in the sawing step.

* * * * *

UNITED STATES PATENT AND TRADEMARK OFFICE
CERTIFICATE OF CORRECTION

PATENT NO. : 5,775,899

DATED : JULY 7, 1998

INVENTOR(S) : HUFFMAN

It is certified that error appears in the above-identified patent and that said Letters Patent is hereby corrected as shown below:

Col. 7, line 42: "sins" should read --pins--

Signed and Sealed this

Fifteenth Day of May, 2001

*Attest:*

NICHOLAS P. GODICI

*Attesting Officer*      *Acting Director of the United States Patent and Trademark Office*